United States Patent
Potuluri et al.

(10) Patent No.: US 8,731,959 B2
(45) Date of Patent: *May 20, 2014

(54) SPECTROSCOPIC CHEMICAL COMPOUND IDENTIFICATION

(75) Inventors: Prasant Potuluri, Raleigh, NC (US); David J. Brady, Durham, NC (US)

(73) Assignee: Optopo Inc., Morrisville, NC (US)

(*) Notice: Subject to any disclaimer, the term of this patent is extended or adjusted under 35 U.S.C. 154(b) by 86 days.

This patent is subject to a terminal disclaimer.

(21) Appl. No.: 12/705,955

(22) Filed: Feb. 15, 2010

(65) Prior Publication Data

US 2010/0209004 A1 Aug. 19, 2010

Related U.S. Application Data (63) Continuation-in-part of application No. 11/609,443, filed on Dec. 12, 2006, now Pat. No. 7,720,694, which is a continuation-in-part of application No. 11/454,923, filed on Jun. 19, 2006, now Pat. No. 7,218,395, which is a continuation-in-part of application No. 10/417,066, filed on Apr. 16, 2003, now Pat. No. 7,092,101, and a continuation-in-part of application No. 11/334,546, filed on Jan. 19, 2006, now Pat. No. 7,301,625.

(60) Provisional application No. 61/152,862, filed on Feb. 16, 2009, provisional application No. 60/725,311, filed on Oct. 12, 2005, provisional application No. 60/811,101, filed on Jun. 6, 2006, provisional application No. 60/644,522, filed on Jan. 19, 2005, provisional application No. 60/705,173, filed on Aug. 4, 2005.

(51) Int. Cl.
*G06Q 10/00* (2012.01)
*G01J 3/42* (2006.01)
*C12Q 1/00* (2006.01)
*G01J 3/04* (2006.01)
*G01J 3/28* (2006.01)

(52) U.S. Cl.
USPC .............. 705/2; 356/326; 435/287.1

(58) Field of Classification Search
USPC .............................................. 705/2
See application file for complete search history.

(56) References Cited

U.S. PATENT DOCUMENTS

| | | | |
|---|---|---|---|
| 5,013,155 A | 5/1991 | Rybak | |
| 6,031,233 A | 2/2000 | Levin et al. | |
| 6,771,369 B2 * | 8/2004 | Rzasa et al. | 356/326 |
| 7,154,102 B2 | 12/2006 | Poteet et al. | |
| 7,218,395 B2 | 5/2007 | Kaye et al. | |

* cited by examiner

*Primary Examiner* — Hiep V Nguyen
(74) *Attorney, Agent, or Firm* — John R. Kasha; Kelly L. Kasha; Kasha Law LLC (57) ABSTRACT

A spectroscopic chemical compound identification system includes a container, a memory, a spectrometer, and a processor. The container receives unknown chemical compound. The memory stores a plurality of spectral signatures corresponding to known chemical compounds. The spectrometer measures a spectral signature of the unknown chemical compound through the container. The processor is connected to the memory and the spectrometer, performs a comparison of the spectral signature with at least one of the plurality of spectral signatures, and determines the identity of the unknown chemical compound from the comparison. The system can be housed in a portable handheld housing. A chemical compound can include a pharmaceutical or controlled substance. The system can be also be used to determine if a pharmaceutical or controlled substance is present within an unknown mixture of chemical compounds.

20 Claims, 5 Drawing Sheets

FIG. 5

SPECTROSCOPIC CHEMICAL COMPOUND IDENTIFICATION

CROSS-REFERENCE TO RELATED APPLICATION

This application claims the benefit of U.S. Provisional Patent Application No. 61/152,862, filed Feb. 16, 2009 and is a continuation-in-part application of U.S. patent application Ser. No. 11/609,443, filed Dec. 12, 2006 now U.S. Pat. No. 7,720,694 (the "'443 application"). The '443 application is a continuation-in-part application of U.S. patent application Ser. No. 11/454,923 (the "'923 application"), filed Jun. 19, 2006 now U.S. Pat. No. 7,218,395 (the "'395 patent"). The '923 application is a continuation-in-part application of U.S. patent application Ser. No. 10/417,066, filed Apr. 16, 2003 now U.S. Pat. No. 7,092,101 (the "'101 patent"), and a continuation-in-part application of U.S. patent application Ser. No. 11/334,546 (the "'546 application"), filed Jan. 19, 2006 now U.S. Pat. No. 7,301,625 (the "'625 patent). The '923 application also claims the benefit of U.S. Provisional Patent Application No. 60/725,311, filed Oct. 12, 2005, and U.S. Provisional Patent Application No. 60/811,101, filed Jun. 6, 2006. The '546 application claims the benefit of U.S. Provisional Patent Application No. 60/644,522, filed Jan. 19, 2005, and U.S. Provisional Patent Application No. 60/705,173, filed Aug. 4, 2005. All of the above mentioned applications are incorporated by reference herein in their entireties.

BACKGROUND OF THE INVENTION

1. Field of the Invention

Embodiments of the present invention relate to systems and methods for identifying pharmaceuticals or controlled substances. More particularly, embodiments of the present invention relate to systems and methods for identifying pharmaceuticals or controlled substances, or determining if pharmaceuticals or controlled substances are present in a chemical compound using spectroscopic analysis and/or machine vision.

2. Background Information

When a patient is admitted to a hospital, the patient may bring along one or more medications they are taking. Generally, the hospital will not allow the patient to take the medications they have brought. Instead, they will verify the prescription, have one of their physicians prescribe the same pharmaceuticals, and dispense the new pharmaceuticals from their own pharmacy. Hospitals do allow patients to use the pharmaceuticals they brought, because they cannot verify that what the patient brought is what was prescribed. In other words, hospitals cannot easily identify a pharmaceutical that a patient brings with them to the hospital.

Similarly, when a patient presents at an emergency room, the patient may bring along a pharmaceutical, controlled substance, or chemical compound that was recently taken. The medication a patient brings can be helpful and sometimes crucial in helping to treat the patient. Unfortunately, pharmaceuticals, controlled substances, or chemical compounds are not easily identified in an emergency room setting.

In view of the foregoing, it can be appreciated that a substantial need exists for systems and methods that can perform pharmaceutical, controlled substance, or chemical compound identification quickly, easily, and accurately in any setting.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION

A system for communicating pharmaceutical verification information across a network is described in the '443 application. This pharmaceutical verification information includes at least one known spectral signature of a known pharmaceutical that is sent to an automatic prescription verification system across the network.

An automatic prescription verification system that uses spectroscopic analysis is described in the '395 patent. A system of the '395 patent uses a static multimode multiplex spectrometer (MMS). A static MMS is described in the '101 patent. A two-dimensional (2D) coded aperture static MMS is described in the '625 patent.

According to a system of the '395 patent, a standard prescription bottle or vial containing a pharmaceutical of a prescription is placed in a spectroscopic sensor system. The spectroscopic sensor system excites the Raman-active modes of the pharmaceutical and detects the resulting Raman emission. A spectral signature that is derived from the measurement is compared to one or more spectral signatures of known pharmaceuticals that are stored in a database. If the spectral signature of the pharmaceutical in the vial matches a spectral signature of a known pharmaceutical stored in the database, the pharmaceutical in the vial is identified. If the identity of the pharmaceutical in the vial matches the pharmaceutical of the prescription, the prescription is verified.

A system of the '395 patent may also include an imaging device to assist in uniquely identifying the pharmaceutical in the prescription vial. The spectral and imaging database may contain images of pharmaceuticals showing their size, shape, color and/or texture, or other data characterizing the size, shape, color and/or texture of known pharmaceuticals. For example, certain pharmaceutical tablets are provided in different sizes according to the dose of the pharmaceutical. In these cases, different doses of the same pharmaceutical may have the same spectral signature, such that the spectral signature cannot be used to identify the strength in addition to identifying the pharmaceutical itself. Once the pharmaceutical has been identified, the imaging device can then be used to identify the strength by comparing the size of the prescription tablet to the sizes for different strengths of that pharmaceutical in the spectral and image database. The imaging device can also be used to determine the shape and/or color of the tablets. This data can then be used as a double-check on the identity of the pharmaceutical, or to differentiate between different strengths or forms (tablets, caplets, liquids, pills, capsules, etc.) of the pharmaceuticals.

Embodiments of the present invention include systems and methods for identifying an unknown chemical compound using spectroscopic analysis. In various embodiments, spectroscopic analysis is used in conjunction with machine vision.

Identification of an Unknown Compound

In a pharmacy, a spectroscopic system, such as a system of the '395 patent, can be used to verify that the pharmaceutical in a standard prescription vial matches the pharmaceutical of a prescription. Such a system can perform verification of pharmaceuticals in a number of different types and sizes of prescription vials, provided that these prescription vials share similar spectroscopic characteristics. As a result, the prescription vial is not generally part of the system. Instead, the prescription vial is part of the item being interrogated by the system.

Outside of a pharmacy setting, very little is known and very little can be assumed about a container holding an unknown pharmaceutical or unknown chemical compound that needs to be identified. Consequently, in various embodiments a system for identifying an unknown chemical compound includes a container for receiving the unknown the chemical compound.

Figure 1:
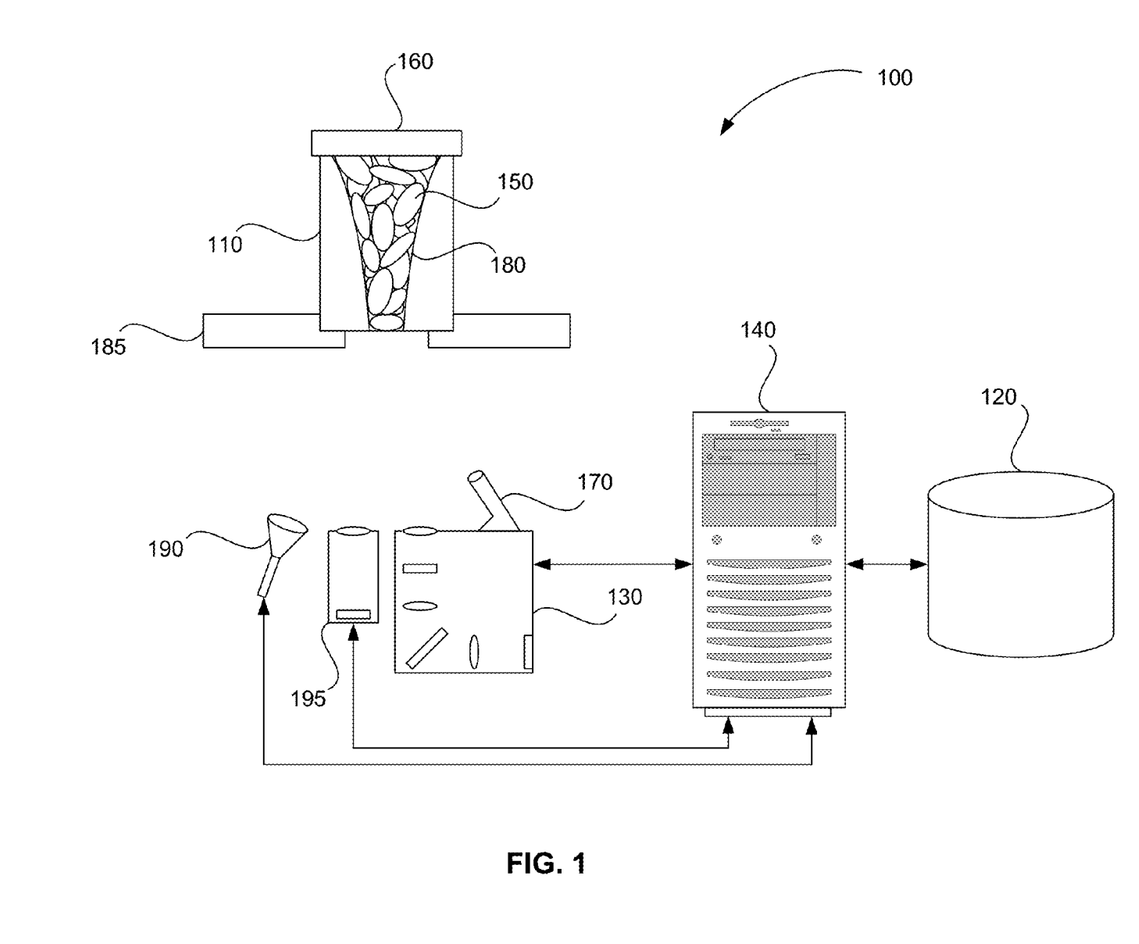
FIG. 1 is a schematic diagram showing a system for identifying an unknown chemical compound, in accordance with various embodiments.

FIG. 1 is a schematic diagram showing a system 100 for identifying an unknown chemical compound 150, in accordance with various embodiments. System 100 includes a container 110, a memory 120, a spectrometer 130, and a processor 140. An unknown chemical compound can be, but is not limited to, a liquid, powder, or solid. Unknown chemical compound 150 as shown in FIG. 1 is, for example, a pharmaceutical solid. A pharmaceutical solid is, for example, a pill. A pill can include, but is not limited to, a tablet, a caplet, a suppository, a gelcap, or a capsule.

Container 110 receives unknown chemical compound 150 from a user. Container 110 includes closed cap 160, for example. In various embodiments (not shown), container 110 can be an open container.

Memory 120 stores a plurality of spectral signatures corresponding to known chemical compounds. Known chemical compounds can include, but are not limited to, pharmaceuticals or controlled substances. Memory 120 can be a volatile or a non-volatile memory. Memory 120 can include, but is not limited to, a hard disk drive, a random access memory (RAM), a read only memory (ROM), a flash memory, or any device capable of storing information.

Spectrometer 130 measures a spectral signature of unknown chemical compound 150 through container 110. Spectrometer 130 measures the spectral signature of unknown chemical compound 150 through the bottom of container 110, for example. In various embodiments (not shown), spectrometer 130 can measure the spectral signature of unknown chemical compound 150 through a side of container 110 or through closed cap 160. Spectrometer 130 is, for example, a multimodal multiplex sampling (MMS) spectrometer. In various embodiments, spectrometer 130 can be a Raman spectrometer.

Spectrometer 130 includes spectrometer light source 170, for example. In various embodiments container 110 is substantially transparent to light transmitted from spectrometer light source 170, reflected from unknown chemical compound 150, and received by spectrometer 130.

Processor 140 is connected to memory 120 and spectrometer 130. Processor 140 performs a comparison of the spectral signature obtained by spectrometer 130 with at least one of the plurality of spectral signatures of known chemical compound stored by memory 120 and determines the identity of unknown chemical compound 150 from the comparison. Processor 140 can include, but is not limited to, a computer, a microprocessor, an application specific integrated circuit, or any device capable of executing a series of instructions.

In various embodiments, container 110 positions unknown chemical compound 150 for analysis by spectrometer 130, if chemical compound 150 is a pharmaceutical solid, for example. Container 110 can include tapered walls 180, for example, to isolate a single pharmaceutical solid or pill as shown in FIG. 1.

In various embodiments, system 100 can include a container handling system 185 that spins container 110 while spectrometer 130 measures the spectral signature of unknown chemical compound 150 through container 110. If container 110 contains multiple pills, spinning container 110 improves identification by decreasing photo-degradation.

In various embodiments, system 100 can include an imaging device light source 190 and an imaging device 195 that are used to capture an image of a pharmaceutical solid of unknown chemical compound 150. Memory 120 stores a plurality of images corresponding to known pharmaceutical solids. Processor 140 performs a comparison of the image captured by imaging device 195 to at least one of the plurality of images stored by memory 120. Processor 140 determines the identity of the pharmaceutical solid of unknown chemical compound 150 from the comparison of the image captured by imaging device 195 to at least one of the plurality of images stored by memory 120 in addition to the comparison of the spectral signature obtained by spectrometer 130 to at least one of the plurality of spectral signatures stored by memory 120.

In various embodiments, container 110 is substantially transparent to light transmitted from imaging device light source 190, reflected from a pharmaceutical solid of unknown chemical compound 150, and received by imaging device 195. Container 110 also positions the pharmaceutical solid of unknown chemical compound 150 for analysis by the imaging device, for example.

In various embodiments, the spectroscopic characteristics of container 110 are known, or container 110 is selected according to its spectroscopic characteristics. In other words, the spectral signature of container 110 is known so that the spectral signature of unknown chemical compound 150 can be disambiguated from the spectral signature measured by spectrometer 130. When spectrometer 130 measures the spectral signature of unknown chemical compound 150 through container 110, this measured spectral signature includes both the spectral signature of unknown chemical compound 150 and the spectral signature of container 110. In order to compare the measured spectral signature to the spectral signatures of known compounds, either the spectral signature of container 110 has to be removed from the measured spectral signature, or the spectral signature of container 110 has to be added to the spectral signatures of the known compounds. Either method, however, requires knowledge of the spectral signature of container 110.

Figure 2:
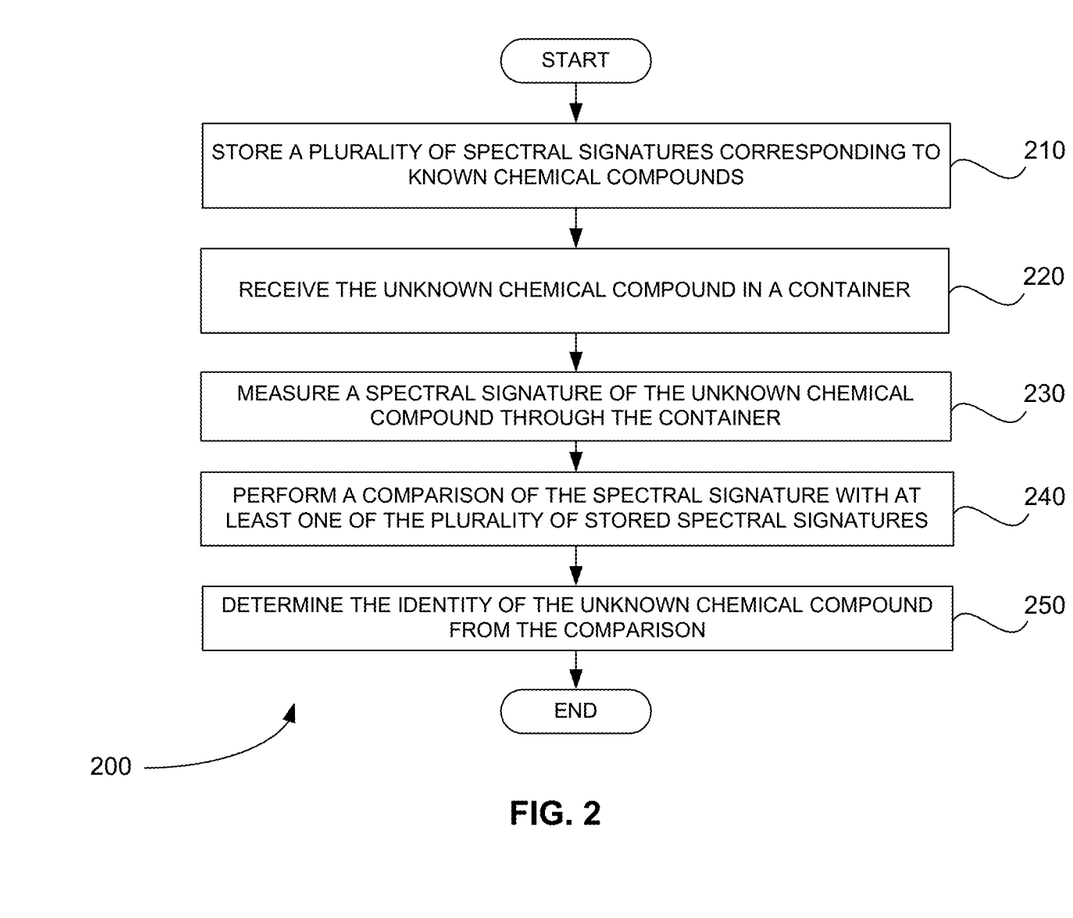
FIG. 2 is a flowchart showing a method for identifying an unknown chemical compound, in accordance with various embodiments.

FIG. 2 is a flowchart showing a method 200 for identifying an unknown chemical compound, in accordance with various embodiments.

In step 210 of method 200, a plurality of spectral signatures corresponding to known chemical compounds is stored.

In step 220, the unknown chemical compound is received in a container.

In step 230, a spectral signature of the unknown chemical compound is measured through the container. In various embodiments, the container is spun while the unknown chemical compound is measured through the container. In various embodiments, the container positions a pharmaceutical solid of the unknown chemical compound for measuring the spectral signature.

In step 240, a comparison of the spectral signature with at least one of the plurality of stored spectral signatures is performed.

In step 250, the identity of the unknown chemical compound is determined from the comparison of the spectral signature with at least one of the plurality of stored spectral signatures.

In various embodiments, method 200 additionally includes storing a plurality of images corresponding to known pharmaceutical solids, capturing an image of a pharmaceutical solid of the unknown chemical compound, performing a second comparison of the image to at least one of the plurality of images, and determining the identity of the pharmaceutical solid from the second comparison in addition to the comparison of the spectral signature with at least one of the plurality of stored spectral signatures. In various embodiments, the container positions the pharmaceutical solid for capturing the image.

In various embodiments of method 200, the steps of identifying the unknown chemical compound take place within a healthcare-related facility or a pharmaceutical related facility. Alternatively, in various embodiments of method 200, the steps of identifying the unknown chemical compound take place within a facility not related to healthcare or pharmaceuticals. A facility not related to healthcare or pharmaceuticals can include, but is not limited to, a forensic facility or a border check facility.

Determination of a Selected Compound in a Mixture

In various embodiments, system 100 shown in FIG. 1 can be used to determine if a pharmaceutical or controlled substance is present within an unknown mixture of chemical compounds. Such a determination can be made independent of the strength of the mixture, dosage form of the mixture, or percentage of excipients in the mixture. In various embodiments, system 100 can include a mode where, if confidence is low for a single chemical compound in the mixture, a search is conducted for a best fit of a binary or ternary mixture of known chemical compounds together with a fit of the approximate percentage amounts of each. Such a mode is useful for narcotics identification where a narcotic is mixed in with a non-narcotic but easily removable diluent such as coffee or sugar granules.

Figure 3:
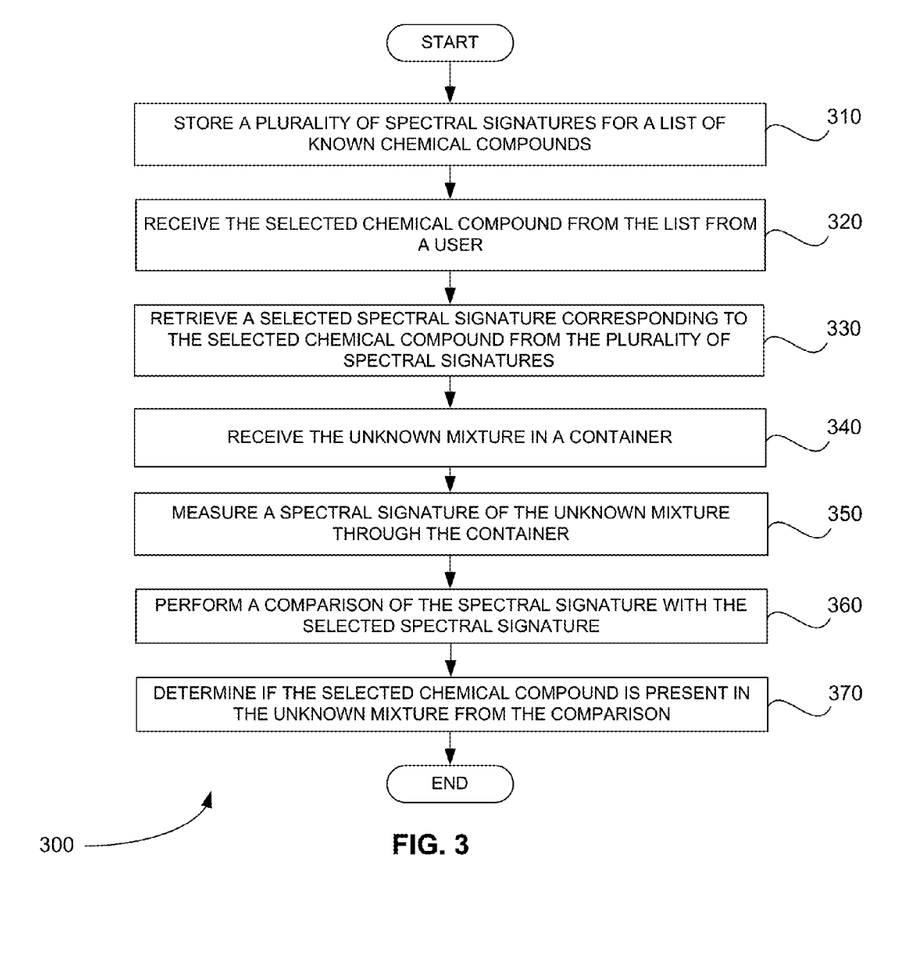
FIG. 3 is a flowchart showing a method for determining if a selected chemical compound is present in an unknown mixture of chemical compounds.

FIG. 3 is a flowchart showing a method 300 for determining if a selected chemical compound is present in an unknown mixture of chemical compounds.

In step 310 of method 300, a plurality of spectral signatures for a list of known chemical compounds is stored.

In step 320, the selected chemical compound from the list is received from a user.

In step 330, a selected spectral signature corresponding to the selected chemical compound is retrieved from the stored plurality of spectral signatures.

In step 340, the unknown mixture is received in a container.

In step 350, a spectral signature of the unknown mixture is measured through the container.

In step 360, a comparison of the spectral signature with the selected spectral signature is performed.

In step 370, if the selected chemical compound is present in the unknown mixture is determined from the comparison.

In various embodiments, a percentage of the selected chemical compound in the unknown mixture is determined from the comparison of the spectral signature with the selected spectral signature.

In various embodiments, two or more selected chemical compounds are selected from the list of known chemical compounds. Two or more selected spectral signatures corresponding to the two or more selected chemical compounds are retrieved from the stored plurality of spectral signatures. A comparison of the measured spectral signature with the two or more selected spectral signatures is performed. If the two or more selected chemical compounds are present in the unknown mixture is determined from the comparison.

In various embodiments, the relative weights or concentrations of the two or more selected chemical compounds is determined from the comparison of the spectral signature with the two or more selected spectral signatures.

Handheld System for Identifying an Unknown Compound

In various embodiments, a portable handheld system can be used to identify an unknown chemical compound. For example, memory 120, spectrometer 130, and processor 140 of FIG. 1 can be housed in a handheld housing (not shown). A spectral signature of unknown chemical compound 150 can be measured in a number of ways. First, an opening of the handheld housing can be placed close to unknown chemical compound 150 so that the light transmitted from spectrometer 130 can be reflected from unknown chemical compound 150 and received at spectrometer 130. The system can use an aiming device (not shown), for example, to properly align the handheld housing and place it at the correct distance from unknown chemical compound 150. The aiming device can include, but is not limited to, a laser range detection device.

Second, the spectral signature of unknown chemical compound 150 can also be measured by placing the unknown chemical compound 150 in a slot in the handheld housing. The slot in the handheld housing places the unknown chemical compound 150 in the correct position and distance from spectrometer 130.

Third, the spectral signature of unknown chemical compound 150 can be measured by placing the unknown chemical compound 150 in container 110 and placing container 110 in container handling system 185, which is also housed in the handheld housing. Container handling system 185, places the unknown chemical compound 150 in the correct position and distance from spectrometer 130.

In various embodiments, a portable handheld system allows a user to create their own database that contains the spectral signatures of some known compounds. The system then identifies whether or not unknown chemical compound 150 is in the user database.

Figure 4:
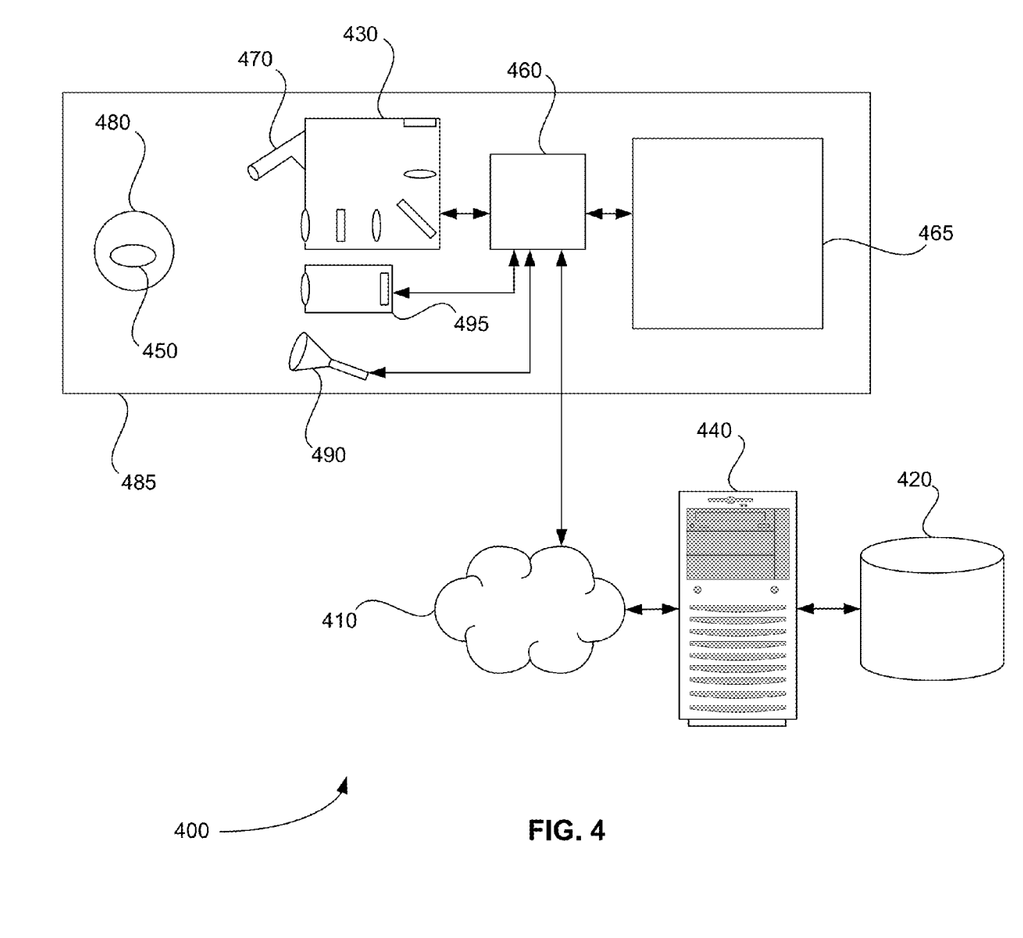
FIG. 4 is a schematic diagram showing a top view of a portable handheld system for identifying an unknown chemical compound, in accordance with various embodiments.

FIG. 4 is a schematic diagram showing a top view 400 of a portable handheld system for identifying an unknown chemical compound, in accordance with various embodiments.

Figure 5:
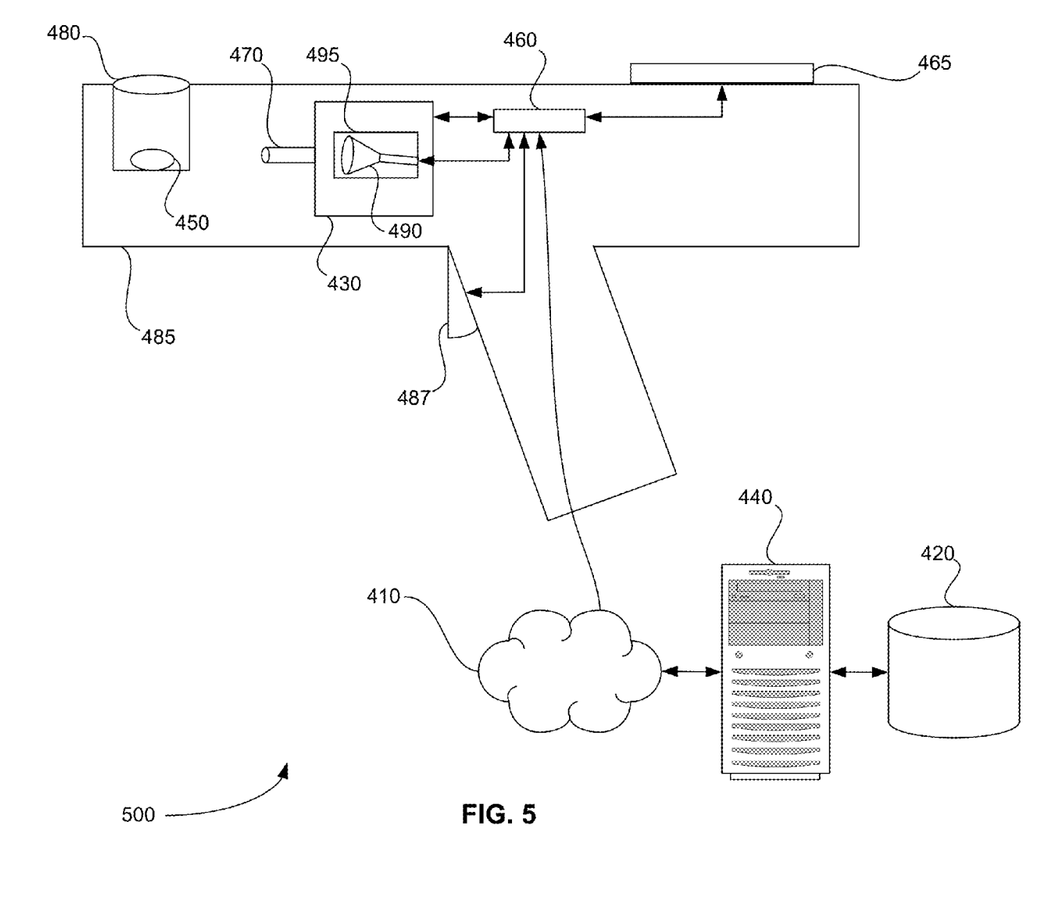
FIG. 5 is a schematic diagram showing a side view of a portable handheld system for identifying an unknown chemical compound, in accordance with various embodiments.

FIG. 5 is a schematic diagram showing a side view 500 of a portable handheld system for identifying an unknown chemical compound, in accordance with various embodiments.

FIGS. 4 and 5 include network 410, processor 440, memory 420, spectrometer 430, spectrometer light source 470, imaging device 495, imaging device light source 490, network adapter 460, display 465, slot 480, and handheld housing 485. Handheld housing 485 houses spectrometer 430, spectrometer light source 470, imaging device 495, imaging device light source 490, network adapter 460, display 465, and slot 480.

Network adapter 460 is in communication with spectrometer 430, spectrometer light source 470, imaging device 495, imaging device light source 490, network adapter 460, display 465, and network 410. Communication can include, but is not limited to, data communication and control communication. Network adapter 460 can include, but is not limited to including, a processor and input/output interface. Network 410 can include, but is not limited to, a local area network, a wide area network, and/or the Internet. Processor 440 is in communication with network 410 and memory 420. Communication to and from network 410 can, for example, be wired or wireless communication.

As shown is FIGS. 4 and 5, the handheld system is used to identify unknown chemical compound 450. Unknown chemical compound 450 is placed in slot 480 and slot 480 places unknown chemical compound 450 at the proper position and distance from spectrometer 430. In various embodiments, slot 480 can include a container handling system (not shown) and unknown chemical compound 450 can be placed in a container (not shown) that is, in turn, placed in the container handling system to properly position unknown chemical compound 450 with respect to spectrometer 430. In various embodiments, housing 485 can alternatively include an opening (not shown) that can be placed in proximity to an unknown chemical compound so that its spectral signature can be measured. As described above, in this embodiment an aiming device (not shown) can be used to position the opening of the handheld system so that the unknown chemical compound is properly positioned with respect to the opening and spectrometer 430.

In FIG. 5, trigger 487, for example, can be depressed to initiate the identification process. When trigger 487 is depressed, network adapter 460 receives a signal prompting it to instruct spectrometer 430 to illuminate unknown chemical compound 450 using spectrometer light source 470 and to measure the spectral signature of light reflected from unknown chemical compound 450. Network adapter 460 then receives the measured spectral signature from spectrometer 430. Network adapter 460 sends the measured spectral signature across network 110 to processor 440. Processor 440 compares the measured spectral signature to a database of spectral signatures of known chemical compounds stored in memory 420.

If the measured spectral signature is found to match a spectral signature in the database of spectral signatures of known chemical compounds, processor 440 transmits information about the identity of the known chemical compound to network adapter 460 across network 410. Network adapter 460 then displays this information about the identity of the known chemical compound on display 465. Information about the identity of the known chemical compound can include, but is not limited to, the name of the known chemical compound, the national drug code (NDC) of the known chemical compound, or an image of the known chemical compound. If the measured spectral signature is not found to match a spectral signature in the database of spectral signatures of known chemical compounds, processor 440 reports the result to network adapter 460 across network 410. Network adapter 460 then displays an indicator that no match was found. Display 465 can also include a touch screen (not shown). The touch screen can be used to receive data or control signals from a user, for example.

In various embodiments, after or before measuring the spectral signature of unknown chemical compound 450, network adapter can signal imaging device light source 490 to illuminate unknown chemical compound 450 and imaging device 495 to capture an image of unknown chemical compound 450. As with the measured spectral signature, network adapter 460 can send the captured image across network 410 to processor 440 for comparison with images of known chemical compounds stored in memory 420. Processor 440 can use the comparison of the captured image with images of known chemical compounds in conjunction with comparison of spectral signatures or independent of the comparison of spectral signatures to determine the identity of unknown chemical compound 450.

In various embodiments, performing spectral and/or image comparisons at a central location across network 410 from a handheld system has a number of advantages. It can reduce the complexity of the handheld system. It can also insure that comparisons are always done with the latest version of a database of known chemical compounds.

In various embodiments, a handheld system can also include a local processor and memory (not shown) for comparing and storing spectral signatures and images. The local processor and memory can be used by a user to collect a local database of known chemical compounds that can be used for comparison with unknown chemical compounds or for updating memory 420.

In various embodiments, a handheld system can include a keypad (not shown). The keypad can be used to receive data or control signals from a user, for example.

In accordance with an embodiment of the present invention, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed. The terms "instructions configured to be executed" and "instructions to be executed" are meant to encompass any instructions that are ready to be executed in their present form (e.g., machine code) by a processor, or require further manipulation (e.g., compilation, decryption, or provided with an access code, etc.) to be ready to be executed by a processor.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for identifying an unknown chemical compound, comprising:
    a memory that stores a plurality of spectral signatures corresponding to known chemical compounds;
    a spectrometer that includes a two-dimensional mask, a dispersive element aligned with the mask that induces a wavelength dependent spatial shift of a two-dimensional image of the mask, and a two-dimensional detector array aligned with the dispersive element that comprises row and column detector elements and that measures a spectral signature of the unknown chemical compound by converting the two-dimensional wavelength dependent spatial shift image of the two-dimensional image of the mask into light intensity values in a single time step using the detector elements; and
    a processor connected to the memory and the spectrometer that performs a first comparison of the spectral signature with at least one of the plurality of spectral signatures and determines the identity of the unknown chemical compound from the first comparison.

2. The system of claim 1, wherein the known chemical compounds comprise a pharmaceutical.

3. The system of claim 1, wherein the known chemical compounds comprise a controlled substance.

4. The system of claim 1, wherein the unknown chemical compound comprises a liquid.

5. The system of claim 1, wherein the unknown chemical compound comprises a powder.

6. The system of claim 1, wherein unknown chemical compound comprises a solid.

7. The system of claim 1, wherein the solid comprises a pharmaceutical solid.

8. The system of claim 7, further comprising a light source and an imaging device that are used to capture an image of the pharmaceutical solid, wherein the memory stores a plurality of images corresponding to known pharmaceutical solids, and wherein the processor performs a second comparison of the image to at least one of the plurality of images and determines the identity of the pharmaceutical solid from the second comparison in addition to the first comparison.

9. The system of claim 7, wherein the pharmaceutical solid comprises one of a pill, a tablet, capsule, a suppository, a gelcap, or a caplet.

10. The system of claim 1, wherein the spectrometer comprises a multimodal multiplex sampling (MMS) spectrometer.

11. The system of claim 1, wherein the spectrometer comprises a Raman spectrometer.

12. The system of claim 1, wherein the memory, spectrometer, and processor are housed in a handheld housing.

13. A method for identifying an unknown chemical compound, comprising:
    storing a plurality of spectral signatures corresponding to known chemical compounds;
    measuring a spectral signature of the unknown chemical compound using a spectrometer that includes a two-dimensional mask, a dispersive element aligned with the mask that induces a wavelength dependent spatial shift of a two-dimensional image of the mask, and a two-dimensional detector array aligned with the dispersive element that comprises row and column detector elements and that measures the spectral signature of the unknown chemical compound by converting the two-dimensional wavelength dependent spatial shift image of the two-dimensional image of the mask into light intensity values in a single time step using the detector elements;
    performing a first comparison of the spectral signature with at least one of the plurality of spectral signatures; and
    determining the identity of the unknown chemical compound from the first comparison.

14. A method for determining if a selected chemical compound is present in an unknown mixture of chemical compounds, comprising:
    storing a plurality of spectral signatures for a list of known chemical compounds;
    receiving the selected chemical compound from the list from a user;
    retrieving a selected spectral signature corresponding to the selected chemical compound from the plurality of spectral signatures;
    measuring a spectral signature of the unknown mixture using a spectrometer that includes a two-dimensional mask, a dispersive element aligned with the mask that induces a wavelength dependent spatial shift of a two-dimensional image of the mask, and a two-dimensional detector array aligned with the dispersive element that comprises row and column detector elements and that measures the spectral signature of the unknown chemical compound by converting the two-dimensional wavelength dependent spatial shift image of the two-dimensional image of the mask into light intensity values in a single time step using the detector elements;
    performing a comparison of the spectral signature with the selected spectral signature; and
    determining if the selected chemical compound is present in the unknown mixture from the comparison.

15. The method of claim 14, further comprising determining a percentage of the selected chemical compound in the unknown mixture from the comparison.

16. A system for identifying an unknown chemical compound, comprising:
    a spectrometer that includes a two-dimensional mask, a dispersive element aligned with the mask that induces a wavelength dependent spatial shift of a two-dimensional image of the mask, and a two-dimensional detector array aligned with the dispersive element that comprises row and column detector elements and that measures a spectral signature of the unknown chemical compound by converting the two-dimensional wavelength dependent spatial shift image of the two-dimensional image of the mask into light intensity values in a single time step using the detector elements;
    a network adapter connected to the spectrometer that sends the spectral signature across a network;
    a processor connected to the network that receives the spectral signature and performs a first comparison of the spectral signature with at least one of the plurality of spectral signatures, determines an identity of the unknown chemical compound from the first comparison, and sends the identity of the unknown chemical compound across the network to the network adapter;
    a display connected to the network adapter that displays the identity of unknown chemical compound; and
    a portable handheld housing that houses the spectrometer, the network adapter, and the display.

17. The system of claim 16, wherein the portable handheld housing further houses a slot used to receive the unknown chemical compound and place the unknown chemical compound at the proper position and distance from the spectrometer.

18. The system of claim 17, wherein the portable handheld housing further houses a slot used to hold a container handling system that receives a container that receives the unknown chemical compound, wherein the slot, the container handling system, and the container place the unknown chemical compound at the proper position and distance from the spectrometer.

19. The system of claim 17, wherein the portable handheld housing further houses an opening that allows the spectrometer to illuminate the unknown chemical compound and receive reflected light from the unknown chemical compound.

20. The system of claim 19, further comprising an aiming device housed by the handheld housing that allows the opening to be positioned at the proper position and distance from the unknown chemical compound.

\* \* \* \* \*